(12) United States Patent
Kitchen

(10) Patent No.: US 7,604,653 B2
(45) Date of Patent: Oct. 20, 2009

(54) SPINAL CURVATURE CORRECTION DEVICE

(76) Inventor: Michael S. Kitchen, 728 Willowlake Rd., Charleston, SC (US) 29412

( * ) Notice: Subject to any disclaimer, the term of this patent is extended or adjusted under 35 U.S.C. 154(b) by 681 days.

(21) Appl. No.: 10/829,766

(22) Filed: Apr. 22, 2004

(65) Prior Publication Data

US 2004/0215191 A1    Oct. 28, 2004

Related U.S. Application Data

(60) Provisional application No. 60/465,340, filed on Apr. 25, 2003, provisional application No. 60/470,149, filed on May 13, 2003.

(51) Int. Cl.
*A61B 17/70* (2006.01)
(52) U.S. Cl. ..................... 606/257
(58) Field of Classification Search ............ 606/61, 606/254–262, 279; 174/95, 113 R
See application file for complete search history.

(56) References Cited

U.S. PATENT DOCUMENTS

| | | | | |
|---|---|---|---|---|
| 3,710,007 | A | * | 1/1973 | Hoeg et al. ............ 174/120 AR |
| 3,823,255 | A | * | 7/1974 | La Gase et al. .......... 174/113 R |
| 4,653,481 | A | | 3/1987 | Howland et al. |
| 4,743,260 | A | | 5/1988 | Burton |
| 5,282,863 | A | | 2/1994 | Burton |
| 5,658,286 | A | | 8/1997 | Sava |
| 5,704,936 | A | * | 1/1998 | Mazel .................. 606/61 |
| 6,184,473 | B1 | * | 2/2001 | Reece et al. ............ 174/110 R |
| 6,241,730 | B1 | | 6/2001 | Alby |
| 6,476,326 | B1 | * | 11/2002 | Fuzier et al. ............ 174/95 |
| 6,554,831 | B1 | | 4/2003 | Rivard et al. |
| 6,706,044 | B2 | | 3/2004 | Kuslich et al. |
| 6,761,719 | B2 | * | 7/2004 | Justis et al. ............ 606/61 |
| 2001/0037111 | A1 | | 11/2001 | Dixon et al. |
| 2002/0082598 | A1 | | 6/2002 | Teitelbaum |
| 2003/0171749 | A1 | | 9/2003 | Le Couedic et al. |
| 2003/0191470 | A1 | | 10/2003 | Ritland |
| 2004/0015167 | A1 | | 1/2004 | Farkas et al. |

FOREIGN PATENT DOCUMENTS

| | | |
|---|---|---|
| FR | 2 702 363 A1 | 3/1993 |
| FR | 2702363 A1 | 3/1993 |
| FR | 2 745 706 A1 | 3/1996 |
| FR | 2806615 A1 | 3/2000 |
| GB | 2 294 394 A | 5/1996 |
| WO | WO 93/20771 | 10/1993 |
| WO | WO 00/16710 | 3/2000 |

* cited by examiner

*Primary Examiner*—Thomas C Barrett
*Assistant Examiner*—Michael J Araj
(74) *Attorney, Agent, or Firm*—B. Craig Killough

(57) ABSTRACT

A spinal curvature correction device has a flexible tube having one or multiple lumens extending longitudinally through substantially the entire length of the flexible member. The lumens are a plurality of channels formed to receive multiple longitudinal members, or rods. Each rod is shaped to a desired curvature of a healthy spine or a curvature that will affect a correction of a diseased spine. The hollow, flexible tube is surgically placed along the axis of the spine and fixed. After fixation to the spinal elements is structurally stable, a plurality of curved semi-rigid rods is placed within the channels of the flexible tube. As additional rods are placed within the hollow flexible member, increased force is applied to the spine by the device, thereby moving the spine towards the desired curvature.

23 Claims, 5 Drawing Sheets

SPINAL CURVATURE CORRECTION DEVICE

This application claims the benefit of U.S. Provisional Application Ser. No. 60/465,340 filed Apr. 25, 2003 and this application claims the benefit of U.S. Provisional Application Ser. No. 60/470,149 filed May 13, 2003.

FIELD OF THE INVENTION

This invention relates to devices and processes used to mollify, correct or improve improper spinal curvature, or to augment strengthen or replace structural components of the mammalian spine that have become lost or dysfunctional.

BACKGROUND OF THE INVENTION

Degenerative and congenital disease states of the human spine are generally characterized by changes in the anatomic relationship between vertebral segments such that there is a geometric variance from "normal". Degenerative changes often involve disruption or loss of normal soft tissue associated with the spinal column. Additionally, loss of bone density and changes in absolute geometry of boney spinal elements are often a component of degenerative disease processes that will require surgical treatment. Various fixation devices consisting of rod or plate mechanisms have been applied to the human spine in attempting to correct these deformities and re-approximate diseased anatomy towards "normal". Most previous designs have rigid structural properties wherein fusion of spinal segments has been the mode of treatment. Additionally, the procedures required for placement of these devices have generally required an open technique with large incisions and commensurate denervation of paraspinus musculature.

Recent developments in spinal instrumentation have emphasized a path towards advancement in percutaneous placement of rod structures, specifically to address the issue of preserving innervation to the paraspinus muscles. Current percutaneous rod systems are generally limited to two or less spinal segments, largely due to the rigid structural property of conventional solid section rods which does not permit deformation for placement nor readily conform to the natural compound curvature of the spine. These systems are almost universally directed towards achieving fusion of the affected spinal segments. The physiologic action of these systems is one of fusion, wherein the device is designed to maximize rigidity between the diseased spinal elements and post-operatively a boney fusion is produced through the normal reparative process and interoperative placement of autologous or artificial bone graft. In essence these systems are directed towards a conventional rigid fixation placed in a percutaneous manner.

Presenting a different approach, several new devices are available that seek to create a physiologic repair that preserves some motion at the instrumented spinal segments; such systems are termed to have properties of "dynamic stabilization". As advances are made in understanding the pathophysiologic processes involved in degenerative spine disease; particularly those processes involved with chronic inflammatory change, devices and process will be implemented that augment native spinal structure while preserving patient motility. A system that can literally "augment" native structure may alleviate much of the pathology of degenerative spine disease. Furthermore, maintaining some degree of motion may offer the patient advantages over older conventional systems that are rigid in nature. Dynamic stabilization systems potentially offer the following advantages: enhanced patient motility that preserves function and improves the level of patient comfort; motion preservation that may reduce post surgical morbidity, in that continued motion at diseased segments can decrease loss of bone density; a construct that provides dynamic stabilization may provide "load sharing" between diseased segments and those adjacent to it; and variable rigidity from one spinal segment to the next, allowing treatment planning to reflect structural needs of each segment taken individually. These principles of "dynamic stabilization" will likely offer a profound advantage over current rigid fixation devices in that there is a reduced probably of the occurrence of adjacent segment degenerative change; prevention of degenerative changes at adjacent segments will likely significantly reduce the probability of re-operation for the patient and reduce the incidence of continued radicular pain post operatively.

There is a need for a device comprised of multiple relatively small cross-sectional rods that form a controlled rigidity structural construct and permit placement in a percutaneous manner. Structural properties of each rod may be varied along its length with varied material composition or size or shape of cross-section. The rods may be made of materials having "memory" properties such that after placement the rods gravitate towards an idealized shape. Each rod can have relatively flexible structural properties allowing significant deformation of the rod to occur during the placement process.

There is a need for a device that is applicable to various disease states of the human spine. Such a device may act as an "internalized splint" that provides continuous distractive or curvature corrective forces well past the time of surgical placement affecting the global geometry of the diseased spine, or exerts an immediate corrective and stabilizing effect upon the degenerative spine at the time of surgery.

Extensive research of the available instrumentation devices available for treatment of juvenile scoliosis has revealed treatment modalities that are largely limited in degree of correction to that which can be obtained at the time of surgery. Furthermore these types of instrumentation are often applied in a manner that seeks to create multiple fusions. Devices of this type cause significant reduction in patient motility and commensurate increased morbidity due to the nature of rigid fixation. An additional limitation to current devices is that they are typically applied after the point or near the point of bone maturity; this limitation effectively delays the time of appropriate treatment and ignores the potential gains that may be realized through bone remodeling. The maximal corrective change of spinal geometry that can be obtained will be dependent upon the ability to initiate correction prior to skeletal maturity.

Conventional rigid fixation devices likewise are not easily exchanged to accommodate changing size as a juvenile patient grows. The techniques of placement with conventional devices often will involve osteotomies of the vertebral bodies thus precluding use in a patient population with significant remaining skeletal growth. There is a need for a device that addresses the issue of patient growth in juveniles, and which provides for longitudinal expansion as the patient develops.

Scoliosis treatment has employed external bracing systems that have been in use for decades, whereby very effective results have been realized. Effective treatment with external bracing modalities however, comes with the caveat of absolute patient compliance. The reality of treatment with bracing has historically fallen significantly below expected results. The primary issue precluding effective treatment using external bracing has been singularly the lack of patient compliance in an adolescent, image conscious population. There is a need for an internalized surgically placed bracing system that precludes failure to wear the device.

Degenerative processes involving the lumbar spine are certainly the largest segment of the spinal instrumentation market. There is a need for a system that is placed percutaneously and affects dynamic stabilization of the spine while spanning greater than two spinal segments. A "load sharing" construct has certain theoretical advantages over currently available systems: adjacent segment degenerative changes may be attenuated or avoided altogether; distribution of loads may break cycles of chronic inflammation and pain so characteristic of lumbar and thoracic pathologies at multiple levels; and ultimately, treatment planning with controlled degrees of rigidity may be applied to different spinal segments thus yielding a greater degree of motility than can be obtained with present rigid fixation systems with uniform structural properties along their length.

SUMMARY OF THE INVENTION

A spinal curvature correction device has a flexible tube having one or multiple lumens extending longitudinally through substantially the entire length of the flexible member. The lumens are a plurality of channels formed to receive multiple longitudinal members, or rods. Each rod is shaped to a desired curvature of a healthy spine.

The hollow, flexible tube is surgically placed along the axis of the spine and fixed. After fixation to the spinal elements is structurally stable, a plurality of curved semi-rigid rods is placed within the channels of the flexible tube. As additional rods are placed within the hollow flexible member, increased force is applied to the spine by the device, thereby moving the spine towards the desired curvature. Additionally, the device is capable of augmenting or replacing endogenous structures of the mammalian spine that have become dysfunctional or lost due to degenerative processes.

DESCRIPTION OF THE DRAWINGS

The first digit of each reference number refers to the Figure number. The next two digits typically represent corresponding elements in each Figure.

DESCRIPTION OF THE PREFERRED EMBODIMENT

Figure 1:
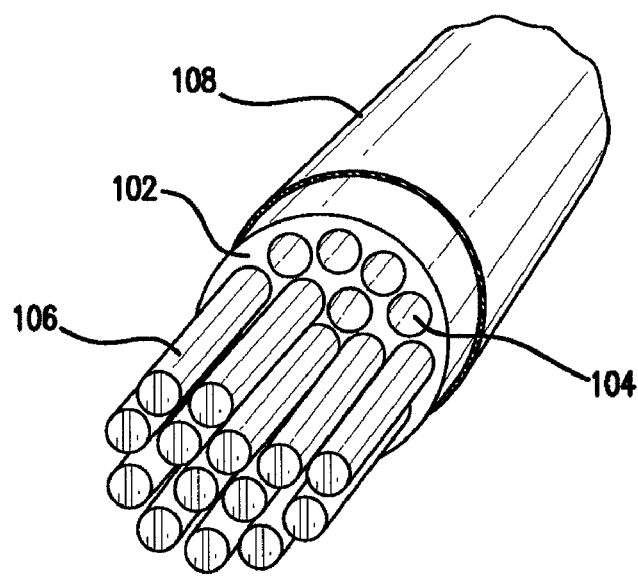
FIG. 1 is a partial view of the device of the present invention showing multiple rods within a multiple lumen flexible tube surrounded with a longitudinally deformable sheath.
Figure 2:
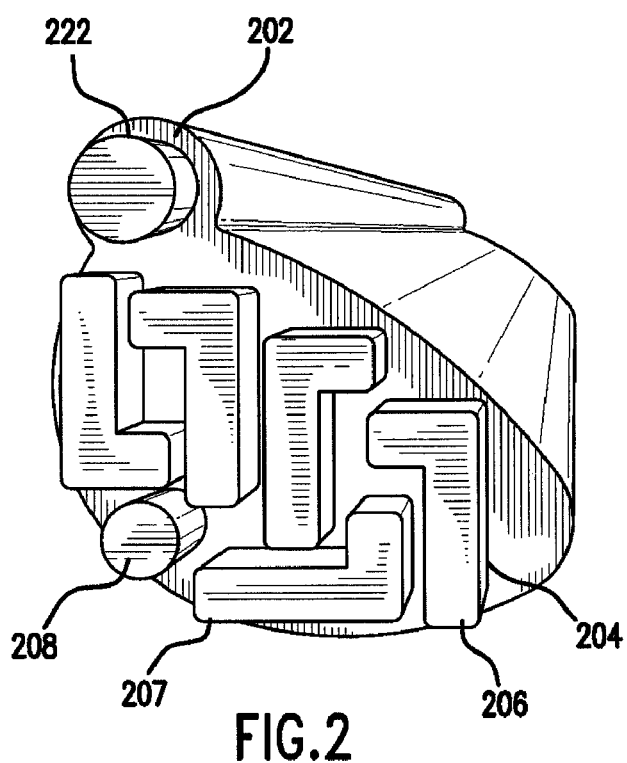
FIG. 2 is a perspective view of an additional embodiment of the device showing a flexible tube having multiple lumens with multiple rods therein.

Turning to the drawings, FIG. 1 and FIG. 2 show a flexible multiple lumen tube 102, 202 wherein a plurality of channels or lumens 104, 204 extend longitudinally through the tube, and preferably, though substantially the entire length of the tube. Each of the channels or lumens is formed to receive, hold and support one or more of semi-rigid rods 106, 206. Each of the channels or lumens holds one or more semi-rigid rod in position within the tube. Each channel is preferred to be in a generally parallel relationship with each immediately adjoining channel. However, individual rods may differ in their orientation from those that are placed adjacent to thereto. Primary structural planes of individual semi-rigid rods may be axially rotated, and are not oriented in a parallel manner to the semi-rigid rods that are adjacent thereto.

Individual rods within the same device may have different cross-sections, with each rod designed to accomplish specific structural requirements, as demonstrated in FIG. 2. The rods as shown have differing orientation and/or cross sectional geometry from one to the other. These characteristics of variable placement and cross-sectional geometry allow the device to have varied degrees of strength in different anatomic planes as desired, thereby inhibiting undesired torsion or other forces on the device. Each semi-rigid rod is deformable when taken individually, but in a preferred embodiment, the overall construct is substantially rigid upon placement of all of the semi-rigid rods within the tube.

Figure 5:
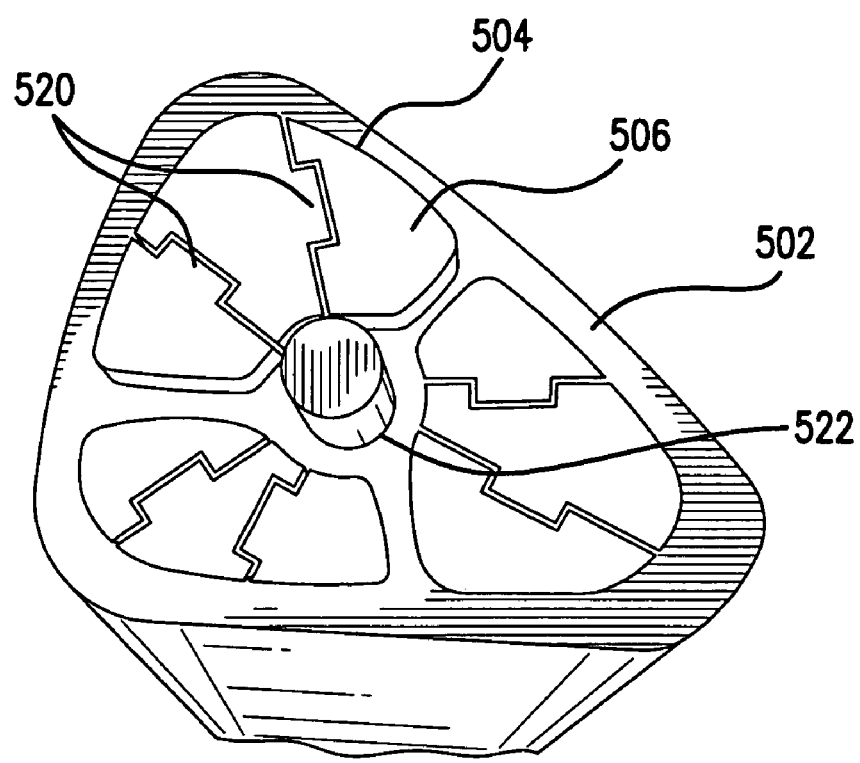
FIG. 5 is a partial view of an additional embodiment of the device of the present invention showing the flexible tube as having multiple lumens and multiple rods therein.

The flexible multi-lumen tube 202, 502 may be asymmetric. FIG. 2; FIG. 5. In one embodiment, a semi-rigid rod 207 is shown having a perpendicularly oriented cross-section relative to the remaining rods.

Figure 3:
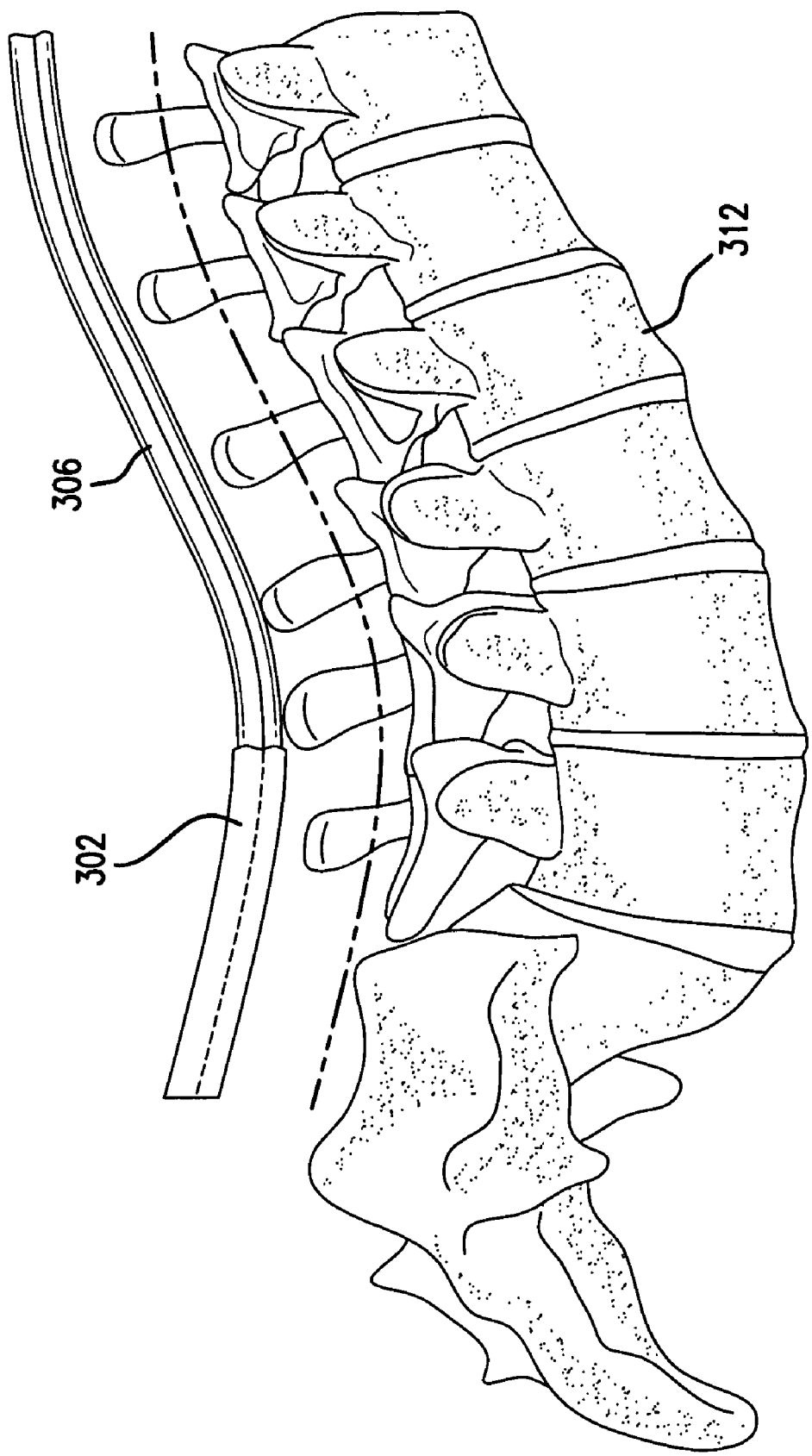
FIG. 3 is a partial view of a human spine demonstrating the device of the present invention relative to the curvature of the spine.

A preferred embodiment comprises a tube 302 and one or more rods 306, and is preferred to be shaped along its length to a desired, or ideal, curvature of a healthy spine 312. FIG. 3. The device places dynamic pressure on the spine to effect, over time, a more normalized shape of the spine.

As shown in FIG. 5 the semi-rigid rods 506 are positioned individually or in small groups into one of the multiple lumens 504 of the flexible tube 502. The plurality of semi-rigid rods collectively have a native curvature conforming to an idealized "normal spine," which forces the overall construct, including the flexible multi-lumen tube, to adopt a geometry approximating normal anatomic curvature FIG. 3. The native or idealized curvature is captured in a material having a memory property, so that the rods urge the spine toward the desired curvature by constantly applying a force, to the spine that is undesirably formed. The amount of the force to be applied may be adjusted as determined by the physician, by placing more or fewer rods within the lumens, which is facilitated by the multiple lumen structure of the tube.

As shown in FIG. 5, the semi-rigid rods 506 engage with profiles of the other rods within the small group. This interdigitated relationship maybe formed as dentils 520, or other similar structures wherein a protrusion engages a receptor in a male-female relationship.

Figure 9:
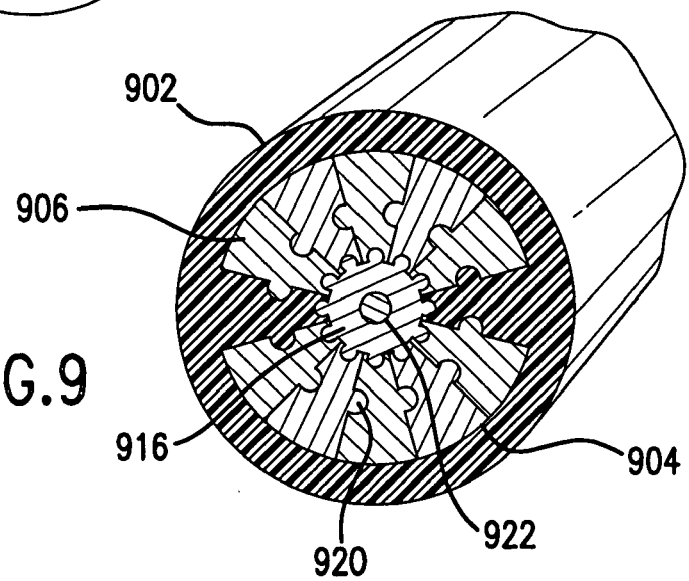
FIG. 9 is a partial view of an embodiment of the device having a single lumen tube and multiple interlocking rods positioned therein.

FIG. 9 shows a protrusion 920 and receptor formed in the rod, wherein the protrusion and receptor are arcuate, with the remainder of the cross section of the semi-rigid rods 906 being pie shaped. The semi rigid rods are structured between other semi-rigid rods and the cross-sectional profile of the receiving lumens 904 in the tube 902, or a central core structure 916, 922. This feature of structural cross-section forms a guide rail for placement of the rods, as well as enhancing the structural properties of the rods when engaged with each other.

Figure 6:
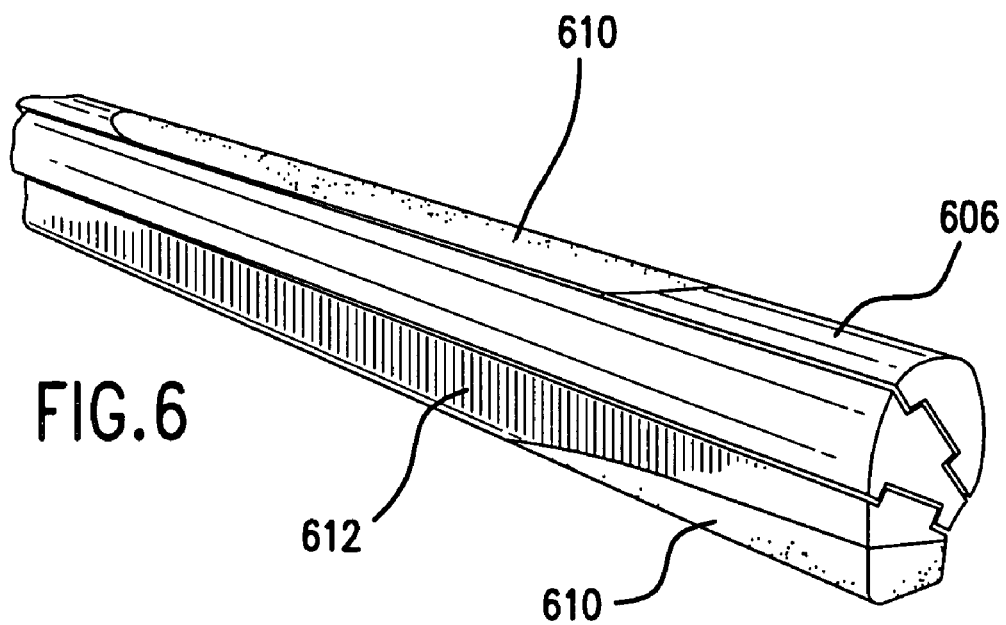
FIG. 6 is a partial view of examples of interlocking rods having variable compositions along their length.
Figure 7:
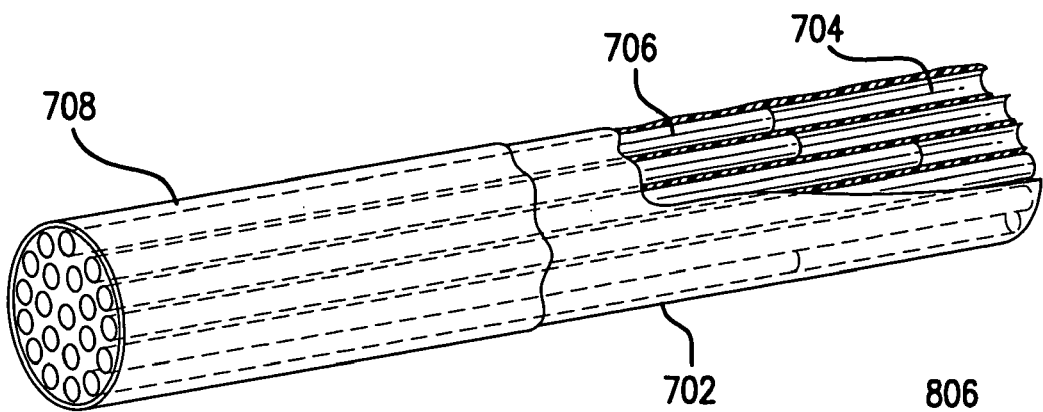
FIG. 7 is a partial view of an embodiment of the device having rods of variable length.
Figure 8:
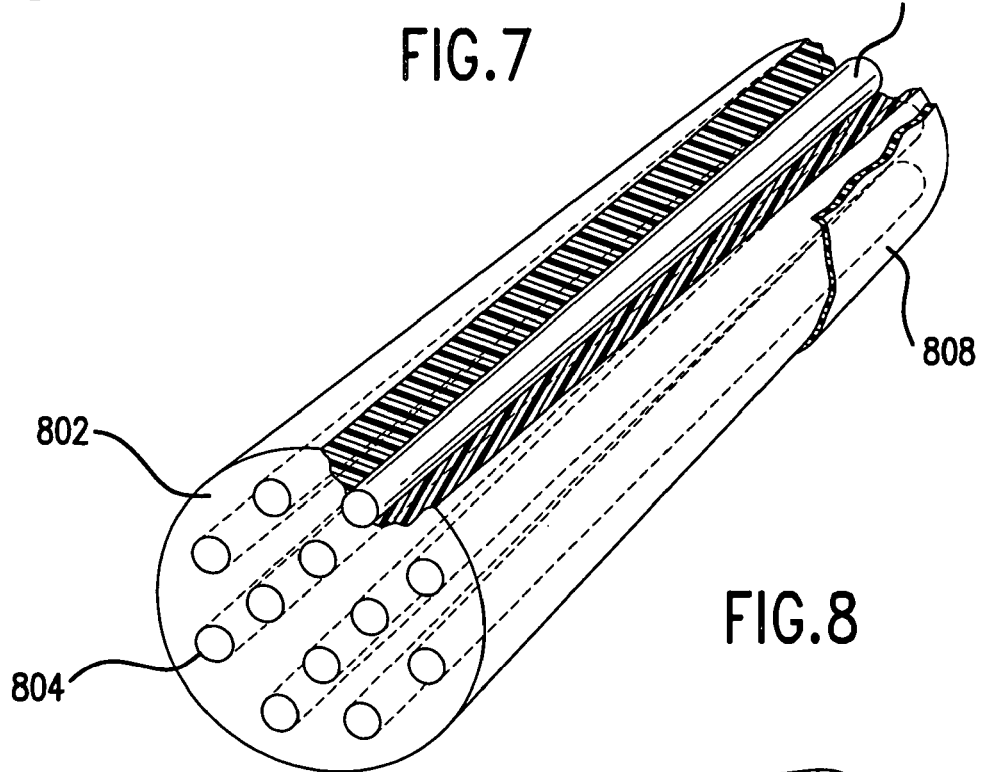
FIG. 8 is a partial view of an embodiment of the device having rods of variable cross sectional dimension along their length.

Additional control of rigidity along the length of the structure may be obtained with a variable cross-section of individual rods. FIG. 8. Variable lengths of the individual rods (FIG. 7), or replacement of some of the structural cross-section of individual rods with materials 610, 612 having differing structural properties from that of the primary material comprising the rod 606 may also be employed (FIG. 6).

The device may also comprise a flexible and longitudinally deformable sheath 108 that is positioned over the flexible multiple lumen tube 102. FIG. 1. A sheath having substantial flexibility, and no less flexibility than the flexible multiple lumen tube, surrounds the flexible multi-lumen tube. The sheath is particularly useful in pediatric applications, where growth and resulting elongation of the spine is anticipated. This allows the sheath, which is deformable longitudinally, to stretch with growth, maintaining a space for subsequent placement of longer multi-lumen tube and semi-rigid rod elements, as is indicated by the patient's growth.

Figure 4:
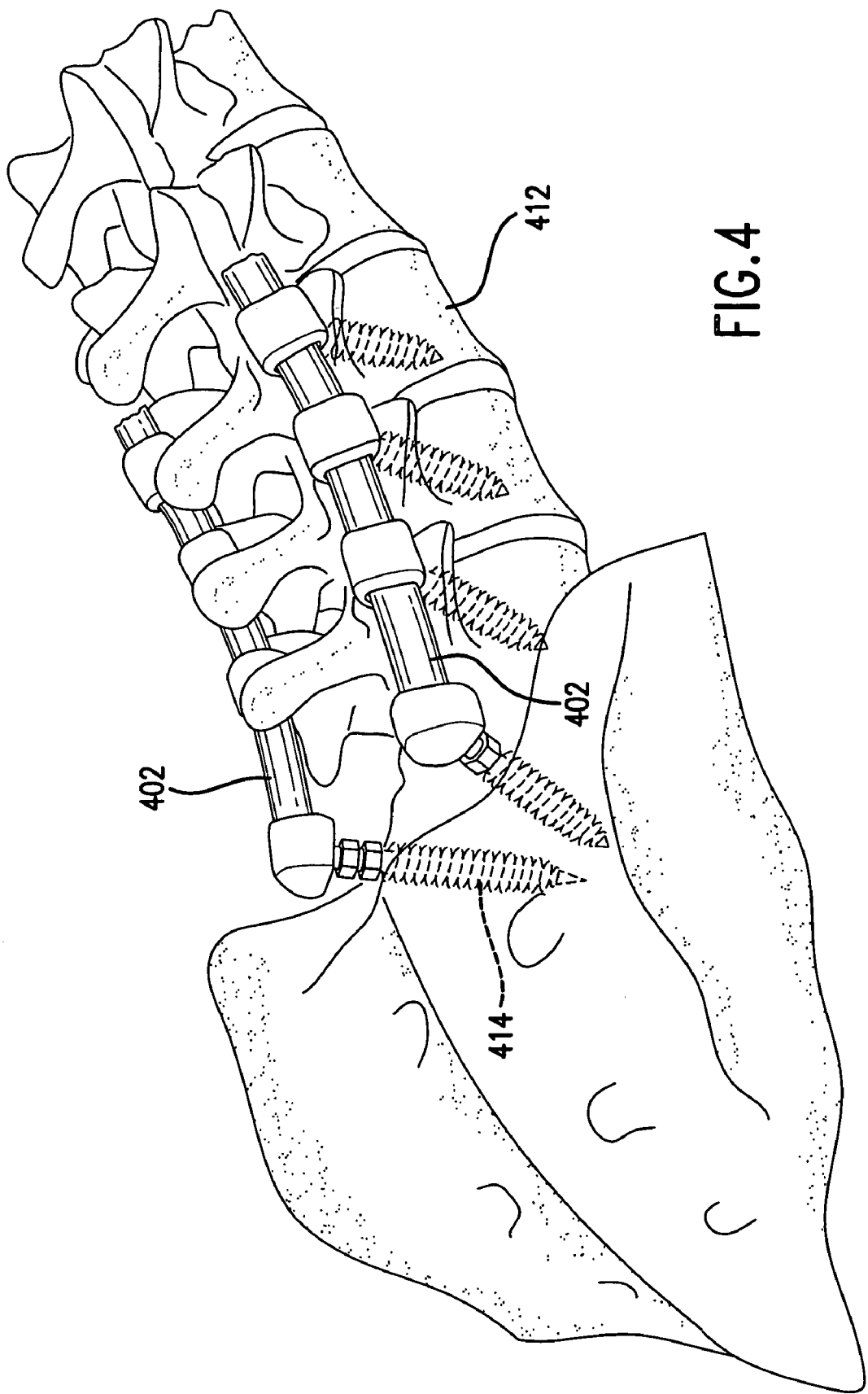
FIG. 4 is a partial view of the human spine having the device of the present invention installed therein.

The device comprises a flexible multiple lumen tube 402 that is placed along the spinal axis of the spine 412 as demonstrated in FIG. 4. The flexible multi-lumen tube is easily deformable and manually bendable at the time of surgery, such that it may be formed to a desired curvature. The flexible multi-lumen tube may be placed over a guide wire to engage the fixation devices, including but not limited to clamps or lamina hooks. It is preferred that that the flexible sheath and flexible multi-lumen tube are surgically placed along the axis of the spine, and fixed to selected individual vertebrae, conforming to the curvature of the diseased spine. After fixation to the spinal elements is structurally stable, a plurality of "ideally" curved semi-rigid rods is placed within the channels of the multiple-lumen flexible tube. Individually, the semi-rigid rod elements are relatively flexible, and are constructed to accommodate the tortuous geometry of a profoundly curved diseased spine, or they are temporarily formed to the shape required for placement at the time of placement within the flexible multiple lumen tube. However, as additional rods are placed within the flexible tube structure, the construct attains a greater degree of rigidity, and an increased level of force is applied to the spine by the collective rods, moving the flexible tube and attachments to the spine towards the "ideal" curvature of a normal spine. FIG. 3. The corrective force of the rod will continue post operatively, effecting a "tendency" to idealized anatomy.

The term "rod" as used herein means an elongated structure. The rod may not have a symmetric cross section, and a rod having a dimension in one axis that exceeds the dimension in the opposite axis may be superior in applying increased force in one direction, while retarding torsion or other undesired movement in another direction. For example, the cross section of the rods 206 shown in FIG. 2 is L-shaped, so that the dimension along one axis is greater than the dimension of the perpendicular axis. Other rods, such as rod 208, may have a symmetrical cross section.

In one embodiment, a longitudinally deformable sheath 108 that is capable of sufficient stretching to accommodate growth of the patient covers the flexible tube. FIG. 1. The longitudinally deformable sheath may be fixed at one or more points to the patient's skeletal axis utilizing conventional clamping mechanisms. The sheath forms and maintains a potential and real space for insertion of the flexible multi-lumen tube and semi-rigid rod structures, while not inhibiting skeletal growth. The flexible sheath structure is separate from the flexible multi-lumen tube and semi-rigid rods, permitting removal and exchange of the flexible multi-lumen tube and semi-rigid rods as the patient grows. Further, the flexible sheath structure permits exchange of the multi-lumen tube and semi-rigid rods to accommodate differing structural requirements, or for replacement in the event of mechanical failure of the flexible multi-lumen tube or any of the semi-rigid rods. The longitudinally deformable sheath will be constructed of highly elastic polymer or conceivably have a plicated surface that allows elongation with minimal resistance to force.

In the embodiments of FIGS. 1, 2 and 5, multiple lumen flexible tubes are shown, with each lumen capable of containing one or more semi-rigid rods. The lumens form the containment for the semi-rigid rods. The flexible multi-lumen tube may comprise a polymer substrate, or similarly deformable material(s), allowing deformation during placement and for accommodating normal or abnormal curvature of the human spine. Once the flexible multi-lumen tube is positioned relative to the spine, it forms a "guide" for introduction of the semi-rigid rods into their respective lumens, and functions as the ongoing containment structure after placement for the semi-rigid rods.

The embodiments of FIGS. 1, 2 and 5 provide means of sequestering wear debris from the device, so that the wear debris is not introduced to the human immune system. The flexible multi-lumen tube structure may be made of biocompatible material that is non-permeable to the immune system and sealed with caps comprised of biocompatible materials after placement of the semi-rigid rods. Alternately, if the flexible multi-lumen tube is of a composite structure the surface that is in contact with tissue may be the only component that requires construction of a biocompatible material. This system effectively prevents exposure of the immune system to wear debris that accumulates through abrasion between semi-rigid rods or the effects of repeated bending of semi-rigid rods. In an instance where both longitudinally deformable sheath and flexible tube are installed, the longitudinally deformable sheath may be made of a non-permeable biocompatable material and assume the role of barrier against exposure to the immune system.

One or more of semi-rigid small caliber rods may be placed within the lumens of the flexible multi-lumen tube structure after surgical placement and fixation of the flexible multi-lumen tube structure. FIGS. 1, 2, 5, 6, 7, and 8. In one embodiment, the individual semi-rigid rods are bent during the process of placement. As the rods are placed, force may be applied manually or with a placement die that will maintain the required curvature for placement through the skin incision and into the individual lumen(s) of the flexible multi-lumen tube. The semi-rigid rods are of small caliber, thus permitting the required temporary deformation to be achieved by applying relatively little force, either manually or with the placement die.

In another embodiment, the semi-rigid rods are of variable geometry along their length, and from rod to rod. Each rod may be of a different cross-section as shown in FIG. 2, with each contributing to the structural properties of the overall device (flexible multi-lumen tube and all semi-rigid rods) when taken collectively. A variable cross-section between the individual semi-rigid rods will additionally allow for spatial considerations of fit to be addressed within the confines of the overall construct cross-section. Rods having asymmetrical cross sections are superior in resisting torsional forces.

In another embodiment, the semi-rigid rods are of variable length, and the length may vary from rod to rod. Each rod 706 within the lumens 704 of the tube 702 may be of a different length, with each rod contributing to the structural properties of the overall device. As in other embodiments, a sheath 708 may be used.

In yet another embodiment, a variable structural section provides variable flexibility along the length of the rod. The variation may be in the absolute cross-sectional area and/or geometry along the length of the semi rigid rods, so that the rod has differing structural properties along its length. FIG. 8 exemplifies this concept by presenting rods 806 within lumens 804 in a tube 802 having a sheath 808, with the rods tapered along their length. Alternately, or a uniform cross-section may be preserved along the length of the rod with selected portions of rod material replaced with "filler" material 610 having minimal structural properties, as shown in FIG. 6. The resulting rod has variable structural properties along its length.

In still another embodiment, a structural cross section of the semi-rigid rods allows for variable flexibility relative to the sagital and coronal planes. Structural cross sections may include "L", "I" or "H" beam geometries. FIG. 2 shows L shaped structural cross sections for rods 206.

A means of attaching the flexible multi-lumen to the spinal axis in a patient may be provided. The device may comprise some or all of the following: longitudinally deformable sheath, flexible multi-lumen tube, semi-rigid rods, and central core. The device may be attached to the human spine utilizing conventional means of clamps and pedicle screws 414 and/or lamina hooks in a conventional manner as demonstrated by FIG. 4. Anatomically, the device is preferred to be placed parallel to the human spine in a longitudinal direction FIG. 4. When the overall construct is of an asymmetric or symmetric cross-section, it works with the clamp mechanism to retard rotation of the device.

Longitudinal movement of all or a portion of the components may be restricted at selected points of attachment. Some applications to specific disease states will benefit from a mechanism that permits some or all of the components to move longitudinally relative to clamps or lamina hooks thus enhancing freedom of motion for the patient in flexion and extension as well as permitting a greater degree of motility for rotation and lateral bending.

The physical characteristics of the multi-lumen tube structure may be manipulated through the selection of materials that afford controlled degrees of compression and/or controlled resistance to tensile forces such that the multi-lumen tube may make a predicable contribution to the structural characteristics of the device. The multi-lumen tube may be of a composite design that exploits the structural characteristics of differing materials within the multi-lumen tube itself. For example, tensile fibers may be cast into a compressible polymer substrate thus exploiting both tensile and compressive structural properties. The structural form may be laminated with methods similar to construction of a tire, thus taking advantage of structural properties of markedly different materials.

A dedicated lumen 222 may be provided in the multi-lumen tube or central core component that will facilitate placement of the tube "over a wire" through annular attachment clamps previously positioned along the spinal axis. FIG. 2. A central lumen 522, 922, may be provided within the flexible tube for engagement of the flexible tube with the guide wire. A needle is threaded through the clamps with a following wire. After the wire is fed through the clamps, successively larger tissue dilators are fed over the wire, creating a space large enough to accommodate the device. The tissue dilators are then removed, and the multi-lumen tube or central core is placed onto the same wire. Once the multi-lumen tube or the central core is in position, the semi-rigid rods are placed by applying a force, such as by using a ram that couples with the introductory end of the multi-lumen tube or central core. The ram may introduce the semi-rigid rods singly, or in groups through a positioning die mechanism.

The flexible multi-lumen tube structure may be arranged in a variety of anatomic locations and oriented along the spinal axis. These locations include, but are not limited to, placement in a trans-pedicular location or placement in an "offset" manner immediately adjacent to the spinus processes through the paraspinus musculature.

This system of spinal fixation, stabilization and anatomic restoration affords the orthopaedic spine surgeon with a high degree of flexibility in treating abnormal curvature of the spine. The device can accommodate a wide range of rigidity by changing the number of rods, the cross-sectional conformation along the length of the rods or their physical properties. The rods can be individualized for each patient, with variability in rigidity, length, and degree of curvature, material composition and shape of curvature.

In one embodiment, the semi-rigid rods are composed of a material having "memory." The material has high strength, and low vulnerability to fatigue. Suitable materials may include, but are not limited to, titanium-nickel alloys (like flexon glasses frames), carbon fibers, or potentially, ceramic carbon fiber materials (like those used in the fabrication of tennis racquets).

This system can be designed so that the rods are accessible after surgery, and replaced with rods having different physical characteristics. Factors such as growth of juveniles, changes in weight in adults, desire to change relative flexibility after a certain therapeutic point is reached, or replacement due to failure or fatigue can be addressed without the necessity of a procedure that is as invasive as the original placement of the device. To accommodate growth in juvenile patients, the longitudinally deformable sheath may allow stretching along its length, wherein relatively rigid points of attachment to the spine are allowed to separate, with little longitudinal resistance.

The device is intended for use in correcting spinal deformities resultant from congenital processes, degenerative processes, trauma, or neoplastic processes. The device exerts an ongoing force that tends towards restoring normal anatomy.

Placement of the device may be accomplished according to currently known surgical techniques for the placement of pedicle screws or lamina hooks that are attached to the spinal axis cephalad at the apex of curvature, and caudally. A potential space is then created along the spinal axis to receive the rod structure. In patients with anticipated growth, the sheath structure is placed through the potential space and secured to the plating structures. Alternately, in patients in whom no further growth is anticipated, the flexible multi-lumen rod structure is placed into the potential space and secured to the plating structures without the sheath.

One application of the device is to substitute the device where previously known rigid rod type devices have been applied. This procedure involves forming a rigid attachment to selected vertebral elements with pedicle screws, lamina hooks or similar devices. Instead of placing and attaching a rigid rod, the flexible multi-lumen tube structure of the invention is used. The flexible multi-lumen tube structure will easily accommodate the abnormal curvature of the diseased spine, and may be firmly affixed by attachment devices.

Multiple flexible multi-lumen tubes may be installed. In this application, the primary function of the flexible multi-lumen tube is to create a pathway for placement of the following semi-rigid rods. The semi-rigid rods, taken singly, allow enough flexibility to bend for placement and follow the path of the flexible multi-lumen tube structure. However, taken as a group, multiple rods allow the entire structure to become rigid, and the device is capable of exerting continuous force directed towards restoring normal anatomy. This system allows for future modification of the device in a minimally invasive manner. Semi-rigid rod components may be changed to allow for patient growth, changing force requirements, or replacement, where fatigue of the rod components has occurred.

The device may be surgically implanted through the paraspinus muscles along the spinal axis, thus avoiding removal of periosteum from the vertebrae and minimizing opportunity for fusion to occur. The implantation may occur "over a wire" placed through points of attachment using a blunt needle.

A clamping structure may be incorporated that limits longitudinal movement of the described structure, thus allowing limited flexibility in all planes for a spine in which the described structures are affixed. The clamping structure may be used to limit longitudinal motion in tension and in compression.

The invention system relies upon independent motion capabilities of individual semi-rigid rods to continuously apply a distractive force. The flexible multi-lumen tube provides lateral stability for the semi-rigid rods, and in so doing, contributes to the overall strength of the system. Regulated freedom of movement for the semi-rigid rods has the additional benefit of allowing the rods to shift slightly when placed under force and to distribute the total load evenly across all of the plurality of rods. The likelihood of fatigue is reduced, as rigid bending points are not present, nor do the rods materially distribute stress to each other.

The longitudinally deformable sheath allows a number of advantages when compared to conventional systems. By virtue of longitudinal deformability, the sheath accommodates growth in pediatric patients. The sheath allows simple changeover of internal structures, including the flexible multi-lumen tube and the semi-rigid rods. A single incision for each rod will allow access to the cap structure, and replacement of the internal components may be accomplished as required. This procedure is anticipated for replacement of rods necessitated as secondary to growth; due to mechanical failure from fatigue; or due to changed structural requirements, including changes of shape, changes of relative rigidity or changes in numbers of rods.

The flexible multi-lumen rod structure may incorporate radio-dense markers that are monitored during growth. The use of markers allows the surgeon to determine when a pediatric patient's rods will over grow the attachment structures, and allows priors replacement. In various embodiments, circumferential radio-dense wires are placed a specific distance from the ends of the rods, radio-dense numerals are placed within the flexible multi-lumen tube, or other radio-dense markers are placed a specified distance from the flexible multi-lumen tube ends.

The device allows for the provision of a lumen in the flexible multi-lumen tube component dedicated for insertion of the flexible multi-lumen tube "over a wire". In one method, a wire is placed using a blunt needle strung between points of spinal fixation. This configuration is applicable at the time of initial placement, as well as facilitating replacement procedures. The wire structure may be tensioned to contribute to force applied towards normalization of curvature. A wire locating member may contribute to the overall structure of the system. In instances where the device is used primarily for posterior stabilization, the wire may provide a "stop" in tension thus limiting flexibility in flexion.

The rods are designed to return a spine to an idealized curvature, and the "memory form" of the rod may be in a shape that is short of, or beyond, the idealized curvature. Additionally, rods may be combined so that the over all effect when placed together is towards an idealized curvature, while individual rods may, in fact, be short of, or beyond, the idealized curvature.

The ease of changeover for rod structures allows the possibility of graduated correction to occur. Rods may be placed in sets each with different properties of curvature and/or rigidity affecting a graduated course of therapy with rods changed as each step in correction is realized.

Cap structures are designed for both cephalad and caudal placement. In pediatric patients, only one end of the rods may be fixed relative to longitudinal movement. This configuration allows growth to occur, and freedom of motion in flexion and extension. Fixation plates will not allow lateral movement at the cephalad or caudal points of fixation. Middle plates may allow swiveling to occur at the rods, thus accommodating movement as the apex of the curvature moves towards ideal. In patients where this device is utilized for posterior stabilization, plating devices are designed to limit motion in flexion and extension.

In a preferred embodiment, when utilized for correction of scoliosis, the sacral attachment provides a basis for alignment of the entire device. Pre-surgical planning is anticipated with defining an ideal axis of alignment from the sacrum. Placement of sacral fixation plates may occur slightly "off axis" of the sacrum to provide idealized alignment of the entire spine.

The multi-lumen flexible tube structure alone provides minimal resistance to deformation. However, as this structure forms a continuous supporting "matrix" for the semi-rigid rods, it contributes to the overall stability of the entire structure, by preventing relative motion between the individual rods, in effect allowing each rod to act as a continuously supported column, with structural moments of each section approximating the diameter or cross-sectional dimensions of the multi-lumen tube structure.

The flexible multi-lumen tube may have a variable cross-section along its length. This configuration allows placement of semi-rigid rods of varying length, thus accommodating variable structural characteristics along the length of the spine.

The semi-rigid rod structures may be of variable length, thus providing greater rigidity as, and where, required. In one configuration the flexible multi-lumen tube may have a greater number of lumens through the lumbar area, and taper towards the thoracic area, thus providing more structural capability in the area of widest cross-section with more semi-rigid rods located in this area.

Methods of Placement

The classic configuration method of placement follows standards of practice currently utilized for placement of Harrington rods or similar devices. This involves an incision medially along the spinal axis with striping of periosteum and paraspinus musculature allowing direct visualization of the facet joints and pedicles. The pedicle screws or lamina hooks are placed under direct visualization and the solid rod is then affixed to the pedicle screws or lamina hooks in an offset or trans-pedicular location using conventional or poly-axial connecting clamps. This procedure typically involves near continuous disruption of the periosteum and significant opportunity for fusion to occur. Additionally, the process of removing the paraspinus musculature from the boney elements of the spine results in muscular denervation and a subsequent level of morbidity following denervation. Although placement utilizing this technique is possible it would likely not be the preferred method of placement in those cases where fusion was deemed undesirable.

A percutaneous method of placement would likely be the preferred method of placement for the majority of cases. Incisions are carried down to the facet joints individually and pedicle screws or lamina hooks are affixed utilizing a port type device that minimizes invasiveness of the procedure while allowing visualization of the boney anatomy. Once the points of attachment are made, clamps may be affixed and secured to the pedicle screws and/or lamina hooks a wire is then percutaneously threaded through the clamps. Ideally the wire is placed with a blunt needle minimizing contact with the bone structures and minimizing stimuli for fusion. Following the wire a tissue dilator is placed over the wire forming a potential space for the rod structures. The tissue dilator is withdrawn leaving the wire in place. The rod structures are then placed over the wire. In one method, the sheath and multi-lumen flexible tube are placed together, followed by individual semi-rigid rods. The individual rods are placed utilizing a ram and a locating die, with alignment assured with a coupling device that attaches to the multi-lumen flexible tube.

The final construct comprised of the multiple rods or multiple rods and flexible multi-lumen tube structure has a structural cross-section with significantly more rigidity that the rods taken individually. This system allows for an essentially rigid construct to be formed or a construct that has a variable degree of rigidity along its length thus forming a dynamic stabilization system allowing for a significant degree of motion along the spinal axis. This system of dynamic stabilization creates an overall construct that facilitates "load sharing" across multiple spinal segments and closely mimics structural characteristics of a normal human spine.

The invention provides for longitudinal expansion of a sheath structure and the ability to change to longer rods and flexible multi-lumen tube as the patient develops. In applications where an exchange of rods and/or flexible tubes is anticipated on a routine basis, the longitudinally deformable sheath is preferred to be provided for encapsulating the flexible tube and rod construct and maintaining a potential space for insertion. The procedure for changing rods and flexible multi-lumen tubes will be minimally invasive, requiring a simple outpatient procedure with a single incision for each rod. Beyond exchanges made for changing rod and flexible tube size the degree of rod "stiffness" may be changed with subsequent placements to accommodate changes in required load or required levels of flexibility as patient weight or need for flexibility changes.

The invention may be placed along the entire thoracolumbar spine in treatment of juvenile scoliosis. A "zero point" of anatomic alignment is established at the sacrum with fixation then established around the apex of deformity and at the upper thoracic region using pedicle screws and clamps. A wire is then threaded through the clamps from thoracic to lumbar and sacral regions, followed by a tissue dilator forming a potential space. The flexible multi-lumen tube structure with longitudinally deformable sheath is then fed over the wire forming a construct for subsequent rod placement. The rods are preformed to an idealized curvature reflecting normal anatomy and after placement into the flexible multi-lumen tube exert a continuous force towards this idealized curvature, affecting correction of anatomic deformity. This process of correction, particularly in scoliosis, relies upon bone remodeling over time to achieve maximal results. Conceivably, for correction of the deformities involved in scoliosis the rods will be placed in a staged process with partial correction obtained with each subsequent set of rods; each set having progressively greater force application realized towards the idealized anatomic curve. Once the therapeutic end result is attained the rods and clamps may be removed, or "stabilization" rods may be placed, affording a greater degree of motility than permitted by "therapeutic" rods.

Treatment of juvenile scoliosis models certain aspects of the invention, however, the device has applicability well beyond scoliosis applications. The ease of placement in a percutaneous manner, with a capacity to span any number of spinal segments, offers a clear advantage over current percutaneous systems. By its very nature as a multi-component structure, the devices has an intrinsic characteristic of scalability, whereby the actual construct may be adapted to specific structural requirements at individual spinal levels. The structural properties of any given installation may be tailored to individual patient needs with detailed treatment planning. Conceivably, computer assisted treatment planning may be applied prior to installation that reflects needs relative to anticipated stresses at different spinal levels and characteristics that conform to specific disease entities. As the field of spinal instrumentation progresses and available devices capable of preserving motion through dynamic stabilization are brought to the market, recognition of adjacent segment degenerative change will have an increasing impact. Devices that are capable of preserving motion and motility will become the standard of care. These devices will minimize limitation of motion at adjacent segments and will be capable of distributing loads across several spinal segments reducing the incidence of adjacent segment degenerative change.

Degenerative pathologies including spondylolysis, spondylolisthesis, kyphosis, retrolisthesis and spondylosis are all amenable to treatment utilizing the invention. Current design configurations allow for placement in an offset manner or trans-pedicular location, and both configurations are amenable to percutaneous placement. Both methods of placement may be effected utilizing conventional clamping systems with poly-axial connections. Offset connections can readily be accomplished with current poly-axial pedicle screw connection designs utilizing specialized clamp systems for those applications with asymmetric rod cross-sections. Placement in a trans-pedicular manner likewise may be accomplished utilizing current poly-axial pedicle screw connections and modified clamps.

Final configurations of this device closely resemble current systems when placed. However, the pedicle screws and clamps may be so positioned that as the rods are advanced into position correction of the deformity can occur. The spatial relationship between clamps may be controlled such that prior to inserting the rods, the clamps are placed reflecting the spinal deformity, and once the rods are inserted forces of distraction, rotation and/or bending will be applied through the clamps directed towards correction of the deformity. The corrective force application of the device is not only realized at the time of placement, but continues throughout the lifespan of the device, causing a gradual correction towards an idealized anatomy. The device may be used concurrently with fusion cages and nuclear implant devices.

In degenerative pathologies, it is anticipated that the largest part of geometric correction will be realized immediately at the time of surgery. However, in congenital deformities and those degenerative states that are characterized by global spinal deformity the force applied by the rods continues long after the time of initial surgery until the spine reaches the desired shape; without the necessity of additional surgeries.

What is claimed is:

1. An implantable, dynamic spinal curvature correction device adapted to correcting the curvature of the spine of a mammalian in need thereof capable of being placed along a longitudinal axis of a mammalian spine, comprising:
   a) a preformed flexible tube of biocompatible material comprising a lumen, wherein said lumen extends longitudinally through said flexible tube, with the outside of said flexible tube being positioned approximate the spine of the mammalian in need thereof; and
   b) a rod comprising a shape memory material having a memorized preformed curvature of an idealized shape prior to surgical placement, wherein said rod is present within said lumen of said flexible tube, and wherein said lumen is formed to receive and hold said rod;
   wherein said lumen of said preformed flexible tube is formed to receive said rod after surgical placement of said preformed flexible tube approximate the spine of the mammalian in need thereof; and wherein, after surgical placement, said memorized preformed curvature of said shape memory material of said rod exerts a dynamic force upon the mammalian spine, and said rod urges said mammalian spine toward the idealized shape.

2. An implantable, dynamic spinal curvature correction device placed along a longitudinal axis of a mammalian spine as described in claim 1 comprising a plurality of rods, each rod comprising a shape memory material having a memorized preformed curvature, wherein each of said plurality of rods is present within only one lumen of said flexible tube.

3. An implantable, dynamic spinal curvature correction device placed along a longitudinal axis of a mammalian spine as described in claim 1 comprising a plurality of rods, each rod comprising a shape memory material having a memorized preformed curvature, wherein at least two of said plurality of rods are present within said lumen of said flexible tube.

4. An implantable, dynamic spinal curvature correction device placed along a longitudinal axis of a mammalian spine as described in claim 1 comprising a plurality of rods each rod comprising a shape memory material having a memorized preformed curvature, wherein said lumen is formed to receive and hold said plurality of rods.

5. An implantable, dynamic spinal curvature correction device placed along a longitudinal axis of a mammalian spine as described in claim 1, wherein said flexible tube comprises a plurality of lumens, wherein said plurality of lumens extends longitudinally through said flexible tube, and comprising a plurality of rods each rod comprising a shape memory material having a memorized preformed curvature, wherein each of said plurality of rods is positioned within one of said plurality of lumens of said flexible tube, and wherein each of said plurality of lumens is formed to receive and hold at least one of said plurality of rods.

6. An implantable, dynamic spinal curvature correction device placed along a longitudinal axis of a mammalian spine as described in claim 1, wherein said rod is manually deformable to a shape other than a preformed memorized curved shape of said rod for placement into said lumen of said flexible tube, and wherein said tube and said rod are positioned in communication with the longitudinal axis of the mammalian spine and place a dynamic force on the mammalian spine.

7. An implantable, dynamic spinal curvature correction device placed along a longitudinal axis of a mammalian spine, as described in claim 1, further comprising a mount that is adapted to mount said flexible tube to the mammalian spine.

8. An implantable, dynamic spinal curvature correction device placed along a longitudinal axis of a mammalian spine as described in claim 7, wherein said longitudinally deformable sheath is substantially impermeable to components of the user's immune system.

9. An implantable, dynamic spinal curvature correction device placed along a longitudinal axis of a mammalian spine as described in claim 8, wherein said implantable, dynamic spinal curvature correction device according to said claim is biocompatible.

10. An implantable, dynamic spinal curvature correction device placed along a longitudinal axis of a mammalian spine as described in claim 1, further comprising a longitudinally deformable sheath that surrounds a length of said flexible tube.

11. An implantable, dynamic spinal curvature correction device placed along a longitudinal axis of a mammalian spine as described in claim 10, wherein said implantable, dynamic spinal curvature correction device according to said claim is biocompatible.

12. An implantable, dynamic spinal curvature correction device placed along a longitudinal axis of a mammalian spine as described in claim 1, wherein said rod is positioned in communication with a longitudinal axis of the mammalian spine and exerts a dynamic force on the mammalian spine and urges said spine toward said memorized preformed shape of said rod.

13. An implantable, dynamic spinal curvature correction device placed along a longitudinal axis of a mammalian spine as described in claim 1, wherein said rod is deformed to a shape that is other than said memorized preformed shape, and wherein said memorized preformed shape is an idealized shape of said spine, and said rod exerts a force on a mammalian spine that is not formed in said idealized shape, and wherein said force is dynamically exerted toward said idealized shape of the mammalian spine.

14. An implantable, dynamic spinal curvature correction device placed along a longitudinal axis of a mammalian spine as described in claim 1, wherein said rod is deformed to a shape that is other than said memorized preformed shape, and wherein said memorized preformed shape is an idealized shape of said spine, and said rod exerts a force on a mammalian spine that is not formed in said idealized shape, and wherein said force is dynamically exerted toward said idealized shape of the mammalian spine for a period of time after installation of said rod in communication with said mammalian spine.

15. An implantable, dynamic spinal curvature correction device placed along a longitudinal axis of a mammalian spine as described in claim 1, wherein said lumen communicates with an end of said flexible tube, and each remaining side of said flexible tube is closed.

16. An implantable, dynamic spinal curvature correction device placed along a longitudinal axis of a mammalian spine as described in claim 15, wherein an end of said flexible tube is covered and said end of said rod is not exposed.

17. An implantable, dynamic spinal curvature correction device placed along a longitudinal axis of a mammalian spine as described in claim 1, wherein said flexible tube is positioned through an incision and over a wire that is longitudinally aligned with said mammalian spine.

18. An implantable, dynamic spinal curvature correction device placed along a longitudinal axis of a mammalian spine as described in claim 1, wherein said lumen of said flexible tube has a guide rail therein, and wherein said rod is positioned within said lumen and along said guide rail.

19. An implantable, dynamic spinal curvature correction device placed along a longitudinal axis of a mammalian spine as described in claim 1, wherein said lumen has at least two rods therein, and wherein said at least two rods are interdigitated with each other.

20. An implantable, dynamic spinal curvature correction device placed along a longitudinal axis of a mammalian spine as described in claim 1, wherein said rod is interdigitated with said flexible tube.

21. An implantable, dynamic spinal curvature correction device placed along a longitudinal axis of a mammalian spine as described in claim 1, wherein an outer surface of said flexible tube is substantially impermeable to components of the user's immune system.

22. An implantable, dynamic spinal curvature correction device placed along a longitudinal axis of a mammalian spine as described in claim 1, wherein said rod of is comprised of varying materials along a length of said rod.

23. An implantable, dynamic spinal curvature correction device placed along a longitudinal axis of a mammalian spine as described in claim 10, wherein said rod has varying structural properties along a length of said rod.

* * * * *